United States Patent
Ding et al.

(10) Patent No.: US 6,184,416 B1
(45) Date of Patent: Feb. 6, 2001

(54) LITHIUM ALUMINATE AS A CATALYST SUPPORT FOR HYDROGENATION OF AROMATIC AMINES

(75) Inventors: Hao Ding, Macungie; John Nelson Armor, Orefield; Lenore Ann Emig, Whitehall; Dorai Ramprasad, Allentown; Gamini Ananda Vedage, Bethlehem; Frederick Carl Wilhelm, Zionsville, all of PA (US)

(73) Assignee: Air Products and Chemicals, Inc., Allentown, PA (US)

( * ) Notice: Under 35 U.S.C. 154(b), the term of this patent shall be extended for 0 days.

(21) Appl. No.: 09/561,071

(22) Filed: Apr. 28, 2000

(51) Int. Cl.⁷ .................................................. C07C 209/00
(52) U.S. Cl. ........................................... 564/450; 564/451
(58) Field of Search ...................... 564/450, 451

(56) References Cited

U.S. PATENT DOCUMENTS

| 2,606,925 | 8/1952 | Whitman ............................... 269/563 |
| 2,606,927 | 8/1952 | Barkdoll et al. ....................... 260/563 |
| 3,636,108 | 1/1972 | Brake ................................ 260/563 D |
| 3,697,449 | 10/1972 | Brake .................................... 252/474 |
| 4,754,070 | 6/1988 | Casey et al. ......................... 564/451 |
| 5,545,756 | 8/1996 | Vedage et al. ........................ 564/450 |

*Primary Examiner*—Samuel Barts
(74) *Attorney, Agent, or Firm*—Russell L. Brewer

(57) ABSTRACT

This invention relates to an improvement in a process for the catalytic hydrogenation of aromatic amines and to the resultant catalyst. The basic process for hydrogenating both mononuclear and polynuclear aromatic amines comprises contacting an aromatic amine with hydrogen in the presence of a rhodium catalyst under conditions for effecting ring hydrogenation. The improvement in the ring hydrogenation process resides in the use of a rhodium catalyst carried on a lithium aluminate support. Often ruthenium is included.

12 Claims, No Drawings

LITHIUM ALUMINATE AS A CATALYST SUPPORT FOR HYDROGENATION OF AROMATIC AMINES

BACKGROUND OF THE INVENTION

Ring hydrogenation of aromatic amines using Group 6 and Group 8 metals carried on a support is well known. Two aspects in the hydrogenation process are problematic. First, contaminants in the aromatic amine substrate can poison the catalyst thus impacting catalyst activity and catalyst life. Second, catalyst attrition can occur thereby resulting in catalyst loss and plugging of catalyst filtration equipment.

Representative patents which illustrate various processes for the hydrogenation of aromatic amines are as follows:

U.S. Pat. Nos. 2,606,925 and 2,606,927 disclose the hydrogenation of nitroaromatics and aromatic amines. The '925 patent shows the use of ruthenium oxide as a catalyst whereas the '927 discloses the use of cobalt on alumina.

U.S. Pat. Nos. 3,636,108 and 3,697,449 disclose the hydrogenation of aromatic compounds and, particularly, 4,4-methylenedianiline to produce a product referred to as PACM, using an alkali metal-moderated ruthenium catalyst. Alkali moderation is accomplished by depositing a ruthenium compound on a support from an aqueous solution of sodium or potassium bicarbonate, hydroxide, or the like. A wide variety of carriers such as calcium carbonate, rare earth oxides, alumina, barium sulfate, kieselguhr and the like are shown as candidate supports. The '449 patent discloses the in situ alkali moderation of the catalyst.

U.S. Pat. No. 4,754,070 discloses an improved process for the hydrogenation of methylenedianiline contaminated with catalyst poisoning impurities. A catalyst comprised of rhodium and ruthenium was found to be effective in the hydrogenation of a crude methylenedianiline, i.e., one containing oligomers. Alkali moderation via addition of lithium hydroxide activation was shown to be effective for the combined catalyst. Carriers suited for the rhodium/ruthenium catalyst included alumina, carbonates, etc.

U.S. Pat. No. 5,545,756 discloses a process for the hydrogenation of aromatic amines, whether mononuclear or polynuclear, using a catalyst of rhodium carried on a titania support. Examples of titania supports include $TiAl_2O_5$, $TiSiO_4$ and $TiSrO_3$. The titania support permitted the use of rhodium alone as the active metal in the hydrogenation of crude methylenedianiline. Rhodium carried on titania in combination with ruthenium on alumina was also suited as a catalyst. Lithium hydroxide activation results in enhanced activity.

BRIEF SUMMARY OF THE INVENTION

This invention relates to an improvement in a process for the catalytic hydrogenation of aromatic amines and to the resultant catalyst. The basic process for hydrogenating both mononuclear and polynuclear aromatic amines comprises contacting an aromatic amine with hydrogen in the presence of a rhodium containing catalyst under conditions for effecting ring hydrogenation. The improvement in the ring hydrogenation process resides in the use of a catalyst comprised of rhodium carried on a lithium aluminate support.

The following represents some of the advantages that can be obtained by the use of the catalysts under specified conditions, they are:

an ability to achieve effective selectivity control to primary amine formation;

an ability to reuse the catalyst over an extended period of time;

an ability to be used in combination with alkali metal reaction promoters without adverse effects;

an ability to tolerate some water through its low solubility in water;

an ability to minimize catalyst loss and product contamination by virtue of excellent attrition resistance; and, an ability to achieve enhanced production through excellent reaction rates.

DETAILED DESCRIPTION OF THE INVENTION

The aromatic amines useful in the practice of the process can be bridged polynuclear aromatic amines or mononuclear aromatic amines. These can be substituted with various substituents such as aliphatic groups containing from 1–6 carbon atoms. Further, the amine group can be substituted with aliphatic groups such as alkyl or alkanol groups resulting in secondary and tertiary amine substituents. Representative mononuclear and polynuclear amines which may be hydrogenated are represented by the formulas:

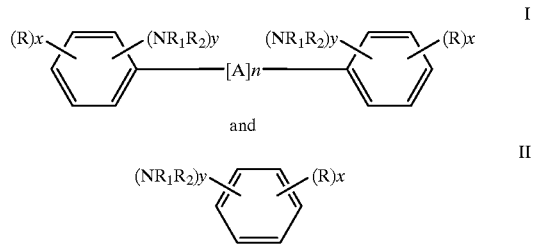

wherein R is hydrogen or C1–6 aliphatic, $R_1$ and $R_2$ are hydrogen, or C1–6 aliphatic, A is C1–4 alkyl, n is 0 or 1, x is 1–3 and y is 1–2 except the sum of the y groups in Formula I excluding A may be 1. When R is hydrogen, then the ring is unsubstituted.

Examples of bridged aromatic amines include methylenedianilines such as bis(para-aminophenyl)methane (PACM) and bis(para-amino-2-methylphenyl)methane; toluidine; bis (diaminophenyl)methane; α, α'-bis(4-aminophenyl-para-diisopropyl benzene(bisaniline P), bis(diaminophenyl) propane (bisaniline A); biphenyl, N—$C_{1-4}$-aliphatic derivatives and N,N'—$C_{1-4}$ aliphatic secondary and tertiary amine derivatives of the above bridged aromatic amines. Examples of mononuclear aromatic amines include 2,4- and 2,6-toluenediamine, aniline, butenyl-aniline derivatives; 1-methyl-3,5-diethyl-2,4 and 2,6-diaminobenzene (diethyltoluenediamine); monoisopropyltoluenediamine, diisopropyltoluenediamine, tert-butyl-2,4- and 2,6-toluenediamine, cyclopentyltoluenediamine, ortho-tolidine, ethyl toluidine, xylenediamine, mesitylenediamie, phenylenediamine and the N and N,N'—C1–4 aliphatic secondary and tertiary amine derivatives of the mononuclear aromatic monoamines and mononuclear aromatic diamines.

Spinel $LiAl_5O_8$ is the preferred support for the catalyst. It is a known composition and known as a support for some catalytic systems. The support is usually made by a solution method wherein an aqueous lithium salt is mixed as a solution with alumina followed by drying and calcination typically in air. Calcination is effected at temperatures in the range from 500 to 1500° C., preferably from about 700 to 1000° C. to ensure the $LiAl_5O_8$ composition. Calcination typical requires at least 10 hours, generally from 20 to 25 hours. In formulating the lithium aluminum support, the level of lithium salt is controlled to provide an atomic ratio of lithium/aluminum ratio of from 0.2 to 1.5 to 5.

The lithium aluminate support can also be made by a solid state reaction between a lithium salt and alumina. As with the solution method, the mixture is dried and then calcined at essentially the same high temperatures over extended periods of time. Lithium salts include LiCl, LiBr, LiF, $Li_2O$, $Li_2SO_4$, $LiNO_3$, LiOH, $Li_2CO_3$, $CH_3COOLi$, HCOOLi with a preference given to $Li_2CO_3$, $LiNO_3$, $CH_3COOLi$. Source of alumina can be chi-alumina, gamma-alumina, eta-alumina, kappa-alumina, delta-alumina, Theta-alumina and alpha-alumina. For economic reasons, lower cost alumina precursors such as gibbsite, boehmite, bayerite, diaspore, can also be used.

A rhodium salt is combined with the lithium aluminate support, based upon its weight as metal, in an amount sufficient to provide a ratio of about 0.1 to 25 weight parts rhodium per 100 weight parts of support. A preferred level is from 2 to 8 weight parts rhodium per 100 weight parts of support. With respect to the preferred catalyst, ruthenium is added to the catalyst with the rhodium to ruthenium weight ratio being from about 1 to 20:1, preferably 6 to 12 weight parts rhodium/weight part ruthenium on the support. Rhodium and ruthenium are added to the support by either incipient wetness or coprecipitation in the presence of a base in water, preferred bases are LiOH, $Li_2CO_3$, or $Na_2CO_3$. The catalyst comprised of rhodium and the lithium aluminate support is dried and heated to a temperature of <400° C.

As with conventional processes the hydrogenation of aromatic amines using the present rhodium catalysts carried on a lithium aluminate support is carried out under liquid phase conditions. Liquid phase conditions are maintained typically by carrying out the hydrogenation in the presence of a solvent. Although as reported in the art, it is possible to effect reaction in the absence of a solvent, the processing usually is much simpler when a solvent is employed. Representative solvents suited for effecting hydrogenation of aromatic amines in the presence of the rhodium metal carried on a lithium aluminate support include saturated aliphatic and alicyclic hydrocarbons such as cyclohexane, hexane, and cyclooctane; low molecular weight alcohols, such as methanol, ethanol, isopropanol; and aliphatic and alicyclic hydrocarbon ethers, such as n-propyl ether, isopropyl ether, n-butyl ether, amyl ether, tetrahydrofuran, dioxane, and dicyclohexylether. Tetrahydrofuran is preferred.

Although in some processes water can be used as a cosolvent, it is preferred that the system be maintained with less than 0.5% by weight. Water, when present in the system, tends to increase the amount of by-product alcohols and heavy condensation products during the hydrogenation process. Also, there is a tendency to deactivate the catalyst system in part by dissolving the support phase. An advantage of the lithium aluminate supported catalyst is that it tolerates the presence of water better than other supported catalysts, even when water content is up to 0.5% by weight.

When a solvent is used, it can be used in concentrations as low as 50% by weight based upon the aromatic amine introduced into the reaction and typically the solvent is used at levels from about 75 to about 200% by weight of the starting compound. Under some circumstances solvent amount as high as 1000 to 2000% based upon the weight of aromatic amine are used.

The hydrogenation of mononuclear and bridged anilines and aromatic amines employs hydrogen partial pressures which range from about 200 to 4000 psig. Preferably the pressure is no higher than 2500 psig and typically can be as low as from about 700 to 1500 psig. Lower pressures are preferred by reason of lower equipment and operating costs. When the pressure is raised toward the upper end of the operating range, higher reaction rates may be achieved but capital costs may override the enhanced productivity benefits.

The ability to ring hydrogenate aromatic amines, and particularly crude methylenedianiline containing from 15 to 20% by weight oligomers, often referred to as MDA 85, at low hydrogenation partial pressures and to simultaneously obtain high conversion with excellent reaction rates and selectivity while minimizing loss to attrition, is achieved by the utilization of a specific catalyst system. Lithium aluminate as a support offers that ability to hydrogenate aromatic amines in the presence of contaminating oligomers as might appear in methylenedianiliine.

In the past, to achieve high selectivity and minimize the formation of amine by-products, while maintaining activity it was proposed that the rhodium and ruthenium component, if present, be alkali moderated. However the lithium aluminate support apparently does not need significant alkali metal hydroxide moderation as do other supports, e.g., alumina and other mixed metal oxide supports. A limited amount of alkali metal hydroxide (preferred at 0.5% or below) may be employed for effective control of the hydrogenation selectivity.

The following examples are intended to illustrate various embodiments of the invention and all parts and percentages given are weight parts or weight percents unless otherwise specified.

EXAMPLE 1

Preparation Of Lithium Aluminate ($LiAl_5O_8$) From Lithium Acetate

Lithium acetate ($CH_3COOLi.2H_2O$, 40.0 g) was added to Gibbsite (C31 alumina 153 g) in a plastic container and mixed. The mixture was then transferred to a ceramic dish and dried at 110° C. for 24 h and calcined at 1000° C. in air for 20 h (ramp: 5° C./min). (Ramp refers to increasing the temperature from room temperature to the final temperature at a specified rate per minute.) Yield: [] 100 g of white powder (XRD indicated $LiAl_5O_8$ with purity over 98%.)

EXAMPLE 2

Preparation Of Lithium Aluminate ($LiAl_5O_8$) From Lithium Carbonate

Lithium carbonate ($Li_2CO_3$, 14.5 g) was added to Gibbsite (C31 alumina from Alcoa, 153 g) in a plastic container and mixed well. The mixture is then transferred to a ceramic dish and calcined at 1000° C. in air for 24 h (ramp: 5° C./min). Yield: [] 100 g of white powder (XRD indicated $LiAl_5O_8$ with purity over 98%.)

Synthesizing $LiAl_5O_8$ by solid state reaction between a lithium salt and aluminum hydroxide eliminates the use of any solvents. This method is especially suitable for large scale synthesis.

EXAMPLE 3

Preparation Of Lithium Aluminate ($LiAl_5O_8$) From Lithium Hydroxide

Lithium hydroxide ($LiOH.H_2O$, 8.25 g) was added to Gibbsite (C31 alumina, 76.6 g) in 40 ml D.I. Water. The free-flow suspension was heated on a hot plate with stirring for 30 min to move water. The resulting solid cake was broken into small pieces and dried in a oven at 110° C. for 16 h. The solid was then ground and calcined at 600° C. (ramp: 5° C./min) for 20 h. Yield: 53 g white powder.

EXAMPLE 4

Hot Water Wash Of $LiAl_5O_8$ 5.0 g of $LiAl_5O_8$ from Example 1 was added to 100 ml of deionized (d.i.) water. The suspension was heated at 85° C. on a hot plate with stirring for 2 h. The remaining solid was collected by filtration and dried at 110° C. for 10 h. 4.8 g of $LiAl_5O_8$ (identified by XRD) was recovered (96% recovery).

EXAMPLE 5
Hot Water Wash Of $LiAl_5O_8$ From Examples 1–3

5.0 g of $LiAl_5O_8$ from Example 3 was added to 100 ml of d.i. water. The suspension was heated at 85° C. on a hot plate with stirring for 2 h. The remaining solid was collected by filtration and dried at 110° C. for 10 h. Only 3.4 g material was recovered (68% recovery).

The results show that the sample of $LiAl_5O_8$ calcined at 1000° C. (Examples 1 and 2) was much more water resistant than the $LiAl_5O_8$ supported catalyst combined at a calcination temperature of 600° C. (Example 3) This is evidenced by the two water wash studies. Recovery of the solid after a hot water wash of $LiAl_5O_8$ calcined at 1000° C. was 96%, compared to a recovery of 68% when it was calcined at 600° C.

EXAMPLE 6
Preparation Of Rh(3%)/ $LiAl_5O_8$ By Coprecipitation Method 7.50 g $LiOH.H_2O$ was added to 400 ml d.i. water (pH=13.2). 100 g $LiAl_5O_8$ was then added to the solution with stirring (pH=13.2). 30.0 g $Rh(NO_3)_3$ solution (Rh wt. %=10.5%, $HNO_3$, [] 15%) was added to the $LiAl_5O_8$ suspension dropwise with stirring. The color of the solution gradually changed from orange red to yellow. The pH is 12.5. The mixture was then heated on a hot plate to 80–85° C. for 30 min. The solution was colorless after heating and final pH is 11.5. The suspension was filtered. The yellow solid cake was collected and dried at 110° C. for 24 h and calcined at 380° C. in air for 6 h. Yield: [] 102 g grayish black powder.

EXAMPLE 7
Preparation Of Rh(3%)/$LiAl_5O_8$ From Incipient Wetness Method 30.0 g $Rh(NO_3)_3$ solution (Rh wt. %=10.5%, $HNO_3$, [] 15%) was added to the $LiAl_5O_8$ (100 g) dropwise with stirring. The resulting brownish yellow solid was dried at 110° C. for 24 h and calcined at 380° C. in air for 6 h. Yield: [] 100 g grayish black powder.

EXAMPLE 8
MDA Hydrogenation Comparisons

General hydrogenation procedure:

A 300 cc autoclave batch reactor was used for this work. All runs were conducted at 180° C. and an 850 psig hydrogen pressure. The solvent was THF. The methylenedianiline (MDA) feed was a 50/50 mixture of 97% MDA and THF. All hydrogenation reactions were carried out at a 1500 rpm stirring rate to minimize hydrogen mass transfer limitations. In the process 0.67 g desired catalyst along with 0.08 g $Ru/Al_2O_3$ was prereduced in the reactor. 100 g of MDA/THF feed was then transferred to the reactor. The system was closed, leak checked and purged three times with nitrogen and then purged three time with hydrogen. The reactor was then pressurized with hydrogen to 850 psig and heated to 180° C. with agitation. (The volume and hydrogen pressure of the ballast were chosen to sufficiently provide all the hydrogen necessary for the reaction without dropping hydrogen pressure below 1000 psig.) When the rate of hydrogen consumption dropped to <2 psig/min, or the ballast pressure reached predetermined level, the reaction was terminated by turning off the heating and closing the hydrogen feed line. Once the reactor reached room temperature, the remaining hydrogen was vented and products were collected by filtration under 100 psig of nitrogen through a charge line containing a 2 $\mu$ filter.

Table 1 shows the condition and results for a series of hydrogenation runs including a comparison with prior art catalysts. In some cases the catalysts were reused to determine catalyst life and, thus, these runs are numerically labeled.

TABLE 1

Hydrogenation of 50% MDA/THF at 180° C., 850 psig pressure of hydrogen, Catalyst loading of 1.5 wt. % on the weight of MDA

| Run | Catalyst[a] | use | T95[b](or TEND) (min) | Conv. (%) | PACM (%) | t/t (%) | Half PACM (%) | Deam Prods (%) | PACM-Sec Amines (%) |
|---|---|---|---|---|---|---|---|---|---|
| 1 | 4% $Rh/Al_2O_3$ US 5,360,934 | 1 | 86 | 96 | 78.6 | 15.3 | 8.4 | 1.7 | 10.3 |
|  |  | 2 | 85 | 99 | 82.2 | 17.0 | 1.9 | 1.6 | 13.2 |
|  |  | 3 | 88 | 99 | 83.6 | 15.5 | 2.5 | 1.4 | 11.7 |
|  |  | 4 | 80 | 99 | 82.7 | 15.6 | 2.6 | 1.4 | 12.5 |
| 2 | 4% $Rh/TiAl_2O_5$[c] | 1 | 100 | 99 | 71.4 | 13.3 | 1.7 | 1.6 | 25.3 |
|  |  | 2 | 110 | 100 | 68.8 | 13.9 | 0.8 | 1.5 | 28.8 |
| 3 | 3% $Rh/TiAl_2O_5$[c] | 1 | 180 | 98 | 76.7 | 13.8 | 4.7 | 1.7 | 16.9 |
| 4 | 3% $Rh/LiAl_5O_8$ (from Ex. 6) | 1 | 155 | 99 | 94.6 | 18.0 | 2.5 | 0.6 | 1.5 |
|  |  | 2 | 74 | 95 | 86.6 | 18.9 | 10.7 | 0.6 | 1.4 |
|  |  | 3 | 61 | 98 | 91.5 | 20.5 | 4.8 | 0.7 | 2.0 |
|  |  | 4 | 57 | 98 | 92.1 | 20.8 | 3.5 | 0.9 | 2.7 |
|  |  | 5 | 59 | 97 | 89.6 | 20.0 | 5.3 | 0.9 | 3.2 |
|  |  | 6 | 57 | 98 | 90.3 | 20.6 | 3.3 | 1.0 | 4.5 |
| 5 | 4% $Rh/LiAl_5O_8$ support from Ex 3 | 1 | 123 | 97 | 90.4 | 17.9 | 6.2 | 0.6 | 1.9 |
|  |  | 2 | 89 | 98 | 89.5 | 17.7 | 4.9 | 0.9 | 3.6 |
|  |  | 3 | 76 | 99 | 88.1 | 17.5 | 2.1 | 1.1 | 7.9 |

TABLE 1-continued

Hydrogenation of 50% MDA/THF at 180° C., 850 psig pressure of hydrogen, Catalyst loading of 1.5 wt. % on the weight of MDA

| Run | Catalyst[a] | use | T95[b](or TEND) (min) | Conv. (%) | PACM (%) | t/t (%) | Half PAC M (%) | Deam Prods (%) | PACM-Sec Amines (%) |
|---|---|---|---|---|---|---|---|---|---|
| | | 4 | 78 | 98 | 81.8 | 16.3 | 4.7 | 1.1 | 11.6 |
| | | 5 | 65 | 98 | 85.1 | 17.9 | 3.5 | 1.1 | 9.5 |

Conv. refers to conversion of methylenedianiline in weight percentage.
Deam Products refer to deaminated methylenedianiline derivatives.
PACM-Sec Amines refer to secondary amines of PACM.
[a]5% Ru/Al$_2$O$_3$ was added such that the Rh:Ru ratio was 10:1
[b]Time for 95% conversion if the conversion is >95%. TEND is the estimated time for 95% conversion if a given conversion is <95%.
[c]data from U.S. Pat. No. 5,545,756, Table 2, Runs 3, 3a & 4.

From Table 1 it is shown that the Rh supported on LiAl$_5$O$_8$ catalyst (Run 4) results in intrinsically higher selectivity to PACM than did the Rh on alumina catalyst (Run 1). While Rh/Al$_2$O$_3$ resulted in 10–13% of PACM secondary amines as byproducts, the Rh/LiAl$_5$O$_8$ catalysts from Examples 3 and 6 generated only 1–5% PACM secondary amines under the same reaction conditions. Such an increase in PACM selectivity was rather surprising since the Rh catalyst supported on mixed metal oxides, i.e., TiAl$_2$O$_5$ generally always resulted in very high percentage of byproducts (such as PACM secondary amines) as shown by Runs 2 and 3. Rh/LiAl$_5$O$_8$ is also more active than Rh/Al$_2$O$_3$. Even with only 3% rhodium, Rh/LiAl$_5$O$_8$ was more active than Rh(4%)/Al$_2$O$_3$.(T95 [] of 80 min vs. [] 60 min). Runs 4 and 5 provide a comparison between supports calcined at 600 and 1000° C. Consistent secondary amine formation is achieved with the catalyst calcined at a temperature of 1000° C. Some secondary amine increases after the first use with the 600° C. calcined catalyst. This is most likely due to some support instability

EXAMPLE 9

Water Sensitivity Testing

A series of runs were conducted to determine the effect of water and LiOH in the hydrogenation reaction and the ability of the rhodium carried on a lithium aluminate support to accommodate water. Table 2 sets forth the results:

TABLE 2

Influence of LiOH addition on hydrogenation of 50% MDA/THF at 180° C., 850 psig pressure of hydrogen, Catalyst loading of 1.5 wt. % on the weight of MDA

| Run | catalyst[a] | use | T95[b] (or TEND) (min) | Conv. (%) | PACM (%) | t/t (%) | External Additives[c] | PACM-Sec Amines (%) |
|---|---|---|---|---|---|---|---|---|
| 1 | 4% Rh/Al$_2$O$_3$ | 1 | 138 | 99 | 86.8 | 18.7 | 2% LiOH/1 g H$_2$O | 6.1 |
| | | 2 | 84 | 98 | 89.3 | 19.0 | 2% LiOH/1 g H$_2$O | 3.8 |
| | | 3 | 101 | 99 | 89.4 | 19.8 | 2% LiOH/1 g H$_2$O | 4.9 |
| | | 4 | 99 | 97 | 84.6 | 19.0 | 2% LiOH/1 g H$_2$O | 5.0 |
| | | 5 | 100 | 93 | 78.9 | 18.0 | 2% LiOH/1 g H$_2$O | 4.8 |
| 2 | 3% Rh/LiAl$_5$O$_8$ (from Ex. 6) | 1 | 79 | 98 | 91.0 | 21.3 | 0.5% LiOH/1 g H$_2$O | 1.8 |
| | | 2 | 97 | 97 | 91.7 | 23.0 | 0.5 g H$_2$O | 1.2 |
| | | 3 | 91 | 97 | 90.6 | 21.6 | 0.5 g H$_2$O | 1.8 |
| | | 4 | 94 | 98 | 92.2 | 21.7 | 0.5 g H$_2$O | 2.1 |
| | | 5 | 98 | 98 | 90.7 | 20.5 | 0.5 g H$_2$O | 2.6 |
| | | 6 | 103 | 97 | 90.6 | 22.4 | 0.5 g H$_2$O | 1.5 |
| | | 7 | 113 | 96 | 88.5 | 21.6 | 0.5 g H$_2$O | 1.8 |

Conv. refers to conversion of methylenedianiline in weight percentage.
Deaminated products refer to deaminated methylenedianiline derivatives.
PACM-Sec Amines refer to secondary amines of PACM.
[a]5% Ru/Al$_2$O$_3$ was added such that the Rh:Ru ratio was 10:1
[b]Time for 95% conversion if the conversion is >95%. TEND is the estimated time for 95% conversion if a given conversion is <95%.
[c]2% LiOH/1 g H$_2$O refers to 2 weight percent of Li as LiOH.H$_2$O in 1 gram of water. The additive solution was added along with MDA feed.
[d]0.5 g H$_2$O refers to the addition of 0.5 gram of water along with MDA feed.

Commentary: In the hydrogenation process, water is always present and often its presence interferes with the effectiveness of LiOH in the PACM secondary amine control. This is particularly true when alumina is used as the catalyst support. The advantage of using lithium aluminate as the catalyst support is demonstrated by the enhanced effectiveness of LiOH as compared to Run 1 even when there is water in the MDA feed (Run 2 verses Run 1). Further control of the PACM secondary amine level was achieved by adding 0.5% LiOH to Rh(3%)/LiAl$_5$O$_8$ catalyst. With merely one addition, the effect of LiOH carried over for the next 6 runs. The PACM secondary amine level was kept at a constant level of [] 2%, (Run 2). By comparison, for the standard Rh(4%)/Al$_2$O$_3$ catalyst, (Run 1) LiOH had to be added for each use and at a higher concentration (2%). The PACM secondary amines level was [] 5%.

What is claimed is:

1. In a process for the catalytic hydrogenation of aromatic amines to their ring hydrogenated counterparts, by contacting the aromatic amine with hydrogen in the presence of a rhodium catalyst carried on a mixed metal support, the improvement which comprises effecting said hydrogenation utilizing a catalyst comprising rhodium carried on a lithium aluminate support.

2. The process of claim 1 wherein the aromatic amine is represented by the formula:

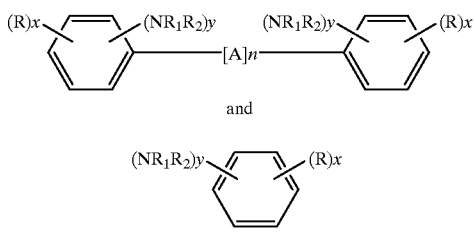

wherein R is hydrogen or C1–6 aliphatic, R$_1$ and R$_2$ are hydrogen, or C1–6 aliphatic, A is C1–4 alkyl, n is 0 or 1, x is 1–3 and y is 1–2 except the sum of the y groups in Formula I excluding A may be 1.

3. The process of claim 2 wherein the aromatic amine is represented by formula 1.

4. The process of claim 3 wherein A is CH$_2$ and n is 1.

5. The process of claim 4 wherein the catalyst is comprised of rhodium and ruthenium carried on a lithium aluminate support.

6. The process of claim 5 wherein weight ratio of rhodium to ruthenium is from 1 to 20:1.

7. The process of claim 6 wherein the hydrogenation pressure is from 200 to 4000 psig.

8. The process of claim 7 wherein the ratio of rhodium to lithium aluminate support is from 2 to 8 weight parts per 100 weight parts support.

9. The process of claim 8 wherein the lithium aluminate support is calcined at a temperature of from 500 to 1500° C.

10. The process of claim 9 wherein the amine is methylene dianiline.

11. The process of claim 10 wherein the hydrogen pressure is from 700 to 1500 psig.

12. The process of claim 1 wherein the lithium aluminate support is calcined at a temperature of from 700 to 1000° C.

* * * * *